United States Patent
Ichinokawa

(10) Patent No.: US 11,039,998 B2
(45) Date of Patent: Jun. 22, 2021

(54) COMPOSITION SUITABLE FOR CLEANSING

(71) Applicant: L'OREAL, Paris (FR)

(72) Inventor: Tomoko Ichinokawa, Kawasaki (JP)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/466,685

(22) PCT Filed: Nov. 22, 2017

(86) PCT No.: PCT/JP2017/042703
§ 371 (c)(1),
(2) Date: Jun. 5, 2019

(87) PCT Pub. No.: WO2018/105450
PCT Pub. Date: Jun. 14, 2018

(65) Prior Publication Data
US 2019/0298639 A1    Oct. 3, 2019

(30) Foreign Application Priority Data

Dec. 8, 2016  (JP) .............................. JP2016-238266

(51) Int. Cl.
| | | |
|---|---|---|
| *A61L 9/012* | (2006.01) | |
| *A61K 8/60* | (2006.01) | |
| *A61K 8/34* | (2006.01) | |
| *A61K 8/37* | (2006.01) | |
| *A61K 8/39* | (2006.01) | |
| *A61K 8/46* | (2006.01) | |
| *A61Q 19/10* | (2006.01) | |
| *A61Q 19/00* | (2006.01) | |
| *A61K 9/50* | (2006.01) | |

(52) U.S. Cl.
CPC .............. *A61K 8/604* (2013.01); *A61K 8/345* (2013.01); *A61K 8/37* (2013.01); *A61K 8/39* (2013.01); *A61K 8/466* (2013.01); *A61K 8/60* (2013.01); *A61K 9/5078* (2013.01); *A61Q 19/00* (2013.01); *A61Q 19/10* (2013.01); *A61K 2800/10* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 2005/0163738 | A1* | 7/2005 | Loifenfeld | ............... A61K 8/31 424/70.1 |
| 2007/0212320 | A1* | 9/2007 | Demitz | ................ A61K 8/8152 424/70.15 |
| 2008/0280797 | A1* | 11/2008 | Compain | ............... A61K 8/042 510/136 |
| 2010/0267598 | A1* | 10/2010 | Sans | ...................... A61K 8/345 510/130 |
| 2015/0335538 | A1* | 11/2015 | Bernard | ................... A61Q 1/14 424/401 |
| 2016/0310396 | A1* | 10/2016 | Terisse | ..................... A61K 8/06 |

FOREIGN PATENT DOCUMENTS

| | | |
|---|---|---|
| JP | 2004-051574 A | 2/2004 |
| JP | 2006-028062 A | 2/2006 |
| JP | 2006-169198 A | 6/2006 |
| JP | 2008-184415 A | 8/2008 |
| JP | 2008-231489 A | 10/2008 |
| JP | 2010-254670 A | 11/2010 |
| JP | 2014-028762 A | 2/2014 |
| JP | 2015-193546 A | 11/2015 |
| KR | 10-2009-0069958 A | 7/2009 |
| WO | 2012/032673 A1 | 3/2012 |
| WO | 2015/067779 A1 | 5/2015 |
| WO | 2015/152420 A1 | 10/2015 |

OTHER PUBLICATIONS

ISA/EP, PCT International Search Report dated Apr. 20, 2018, which was issued in connection with PCT Application No. PCT/JP2017/042703 (2 pages).
EPO, Office Action for the corresponding European patent application No. 17823232.8, dated Oct. 6, 2020.
Database GNPD [Online], MINTEL, "Cleansing Cream", XP055723641, retrieved from www.gnpd.com, Apr. 30, 2008, database accession No. 1212110.
JPO, Office Action for the corresponding Japanese patent application No. 2016-238266, dated Sep. 28, 2020, with English translation.
Tokiwa Pharmaceutical Co., Japan, "Makeup Removing Cream," ID#1623589, Mintel GNPD [online], Aug. 2011, retrieved Aug. 28, 2020, with English brief description of relevance.
JPO, Office Action for the corresponding Japanese patent application No. 2016-238266, dated Apr. 26, 2021, with English translation.
Infinitus, China, "Refreshing Day Emulsion," ID#4178181, Mintel GNPD, Jul. 2016.
KIPO, Office Action for the corresponding Korean patent application No. 10-2019-7019048, dated Mar. 16, 2021, with English translation.

* cited by examiner

*Primary Examiner* — Susan T Tran
(74) *Attorney, Agent, or Firm* — Lucas & Mercanti, LLP

(57) ABSTRACT

A composition contains (a) at least one fatty acid sugar ester; (b) at least one anionic surfactant selected from amino acid surfactants and taurate surfactants; (c) at least one polyoxyalkylenated polyol fatty acid ester having an HLB value of 12 or less; (d) at least one oil; (e) at least one polyol; and (f) water. An embodiment according to the present invention can be stable before being applied onto the skin and provides quick texture transformation after being applied onto the skin, and therefore, is useful as a cleansing product.

13 Claims, No Drawings

COMPOSITION SUITABLE FOR CLEANSING

CROSS-REFERENCE TO RELATED APPLICATIONS

This application is a 371 of PCT/JP2017/042703, filed on Nov. 22, 2017, which claims benefit of Japanese Patent Application No. 2016-238266 filed on Dec. 8, 2016, each of which is hereby incorporated by reference in its entirety.

TECHNICAL FIELD

The present invention relates to a composition including a specific combination of ingredients, in particular a cosmetic composition for the skin, as well as a cosmetic process using the same.

BACKGROUND ART

Cleansing the skin is very important for caring for the face. It must be as effective as possible because greasy residues, such as excess sebum, the remnants of cosmetic products used daily, and make-up products, in particular waterproof products, accumulate in the skin folds, and can block the pores of the skin and result in the appearance of spots.

Several types of skin cleansing products, for example, rinsable cleansing anhydrous oils and gels, and foaming creams, lotions and gels, are known.

Rinsable anhydrous oils and gels have a cleansing action mainly by virtue of oils present in these formulations. These oils make it possible to dissolve fatty residues and to disperse make-up pigments. These products are effective and well tolerated.

D-phase emulsification (Hiromichi Sagitani (1988): Formation of O/W Emulsions by Surfactant Phase Emulsification and the Solution Behavior of Nonionic Surfactant System in the Emulsification Process, Journal of Dispersion Science and Technology, 9:2, 115-129) is one of the methods for preparing emulsions. By using D-phase emulsification technology, emulsions including a small-sized, micro- or nano-sized, dispersed phase can be prepared without mechanical homogenization. Furthermore, as compared with conventional emulsification technology, emulsions prepared by D-phase emulsification can be stabilized by a lesser amount of surfactant(s).

Conventional O/W emulsification technology typically includes the step of agitating water and oil phases with emulsifier(s) or surfactant(s) at elevated temperature, and requires strong mechanical shearing to make oil particles small in size. In contrast, the D-phase emulsification process includes two steps, and provides very fine emulsions without strong mechanical agitation. The first step is the preparation of a D-phase (oil in surfactant: O/D) using surfactant(s), polyol(s), fatty component(s), and a small amount of water. The second step is to form an O/W emulsion by adding a large amount of water to the D-phase.

It is proposed to apply D-phase emulsification to cleansing products. The cleansing products based on D-phase emulsification may be the preparation of a cleansing product by diluting a phase including surfactant(s), polyol, and water, with oil (e.g., JP-A-2006-169198). A composition based on D-phase technology can contain a large amount of oil which contributes to high make-up removability.

DISCLOSURE OF INVENTION

A composition based on D-phase technology can provide unique texture to the skin. If the composition is in the form of a gel, the composition provides a viscous feeling. However, by rubbing the composition with the fingers, the texture of the composition changes, and provides less a viscous feeling as if the composition is in the form of a liquid. This texture transformation is important, because good make-up removability can be realized after the texture transformation. Therefore, it is preferable that the texture transformation occur quickly after the application of the composition onto the skin.

On the other hand, with regard to good stability which is required, for example, for storing compositions such as cleansing products, it is preferable for the composition based on D-phase technology as well to have high viscosity before being applied onto the skin.

Thus, an objective of the present invention is to provide a composition useful as a cleansing product, which can be stable before being applied onto the skin and provides quick texture transformation after being applied onto the skin.

The above objective can be achieved by a composition, comprising:
(a) at least one fatty acid sugar ester;
(b) at least one anionic surfactant selected from amino acid surfactants and taurate surfactants;
(c) at least one polyoxyalkylenated polyol fatty acid ester having an HLB value of 12 or less;
(d) at least one oil;
(e) at least one polyol; and
(f) water.

The fatty acid of the (a) fatty acid sugar ester may be selected from saturated $C_{10}$-$C_{24}$ fatty acids, preferably $C_{10}$-$C_{18}$ fatty acids, and more preferably $C_{12}$-$C_{16}$ fatty acids.

The (a) fatty acid sugar ester may be selected from the group consisting of sucrose laurate, sucrose myristate, sucrose palmitate, sucrose stearate, and mixtures thereof.

The amount of the (a) fatty acid sugar ester in the composition may range from 0.001% to 20% by weight, preferably from 0.01% to 10% by weight, and more preferably from 0.1% to 5% by weight, relative to the total weight of the composition.

The amino acid surfactant may be selected from the group consisting of glutamates, N-acylated glutamates, aspartates, N-acylated aspartates, and salts thereof.

The taurate surfactant may be selected from the group consisting of taurate, caproyl taurate, lauroyl taurate, myristoyl taurate, palmitoyl taurate, stearoyl taurate, oleoyl taurate, cocoyl taurate, methyl taurate, coconut oil fatty acid methyl taurate, palm kernel oil fatty acid methyl taurate, hydrogenated palm kernel oil fatty acid methyl taurate, beef tallow fatty acid methyl taurate, hydrogenated beef tallow fatty acid methyl taurate, caproyl methyl taurate, lauroyl methyl taurate, myristoyl methyl taurate, palmitoyl methyl taurate, stearoyl methyl taurate, oleoyl methyl taurate, cocoyl methyl taurate, methyltaurine cocoyl methyl taurate, and salts thereof.

The amount of the (b) anionic surfactant selected from amino acid surfactants and taurate surfactants in the composition may range from 0.001% to 20% by weight, preferably from 0.01% to 10% by weight, and more preferably from 0.05% to 5% by weight, relative to the total weight of the composition.

The (c) polyoxyalkylenated polyol fatty acid ester may have an HLB value of 6 to 12, preferably 6.5 to 11.5, and more preferably from 7 to 11.

The (c) polyoxyalkylenated polyol fatty acid ester may be selected from POE glyceryl fatty acid esters, preferably from the group consisting of PEG-7 glyceryl cocoate, PEG-8 glyceryl isostearate, PEG-20 glyceryl tri-isostearate, PEG-20 glyceryl stearate, PEG-20 glyceryl isostearate, and mixtures thereof.

The amount of the (c) polyoxyalkylenated polyol fatty acid ester in the composition may range from 0.001% to 20% by weight, preferably from 0.01% to 10% by weight, and more preferably from 0.1% to 5% by weight, relative to the total weight of the composition.

The amount of the (d) oil in the composition may range from 50% to 90% by weight, preferably from 60% to 85% by weight, and more preferably from 70% to 80% by weight, relative to the total weight of the composition.

The amount of the (e) polyol in the composition may range from 0.001% to 20% by weight, preferably from 0.01% to 15% by weight, and more preferably from 0.1% to 10% by weight, relative to the total weight of the composition.

The amount of the (f) water in the composition may range from 0.001% to 20% by weight, preferably from 0.01% to 15% by weight, and more preferably from 0.1% to 10% by weight, relative to the total weight of the composition.

The composition according to the present invention may be a cosmetic composition, preferably a skin cosmetic composition, and more preferably a skin cleansing composition.

The present invention also relates to a cosmetic process for a keratin substance, preferably skin, comprising applying to the keratin substance the composition according to the present invention.

BEST MODE FOR CARRYING OUT THE INVENTION

After diligent research, the inventors have discovered that it is possible to provide a composition, useful as a cleansing product, which can be stable before being applied onto the skin and provides quick texture transformation after being applied onto the skin.

The composition according to the present invention comprises:
(a) at least one fatty acid sugar ester;
(b) at least one anionic surfactant selected from amino acid surfactants and taurate surfactants;
(c) at least one polyoxyalkylenated polyol fatty acid ester having an HLB value of 12 or less;
(d) at least one oil;
(e) at least one polyol; and
(f) water.

The composition according to the present invention has sufficient viscosity before being used, and therefore, can be stable before being applied onto the skin. Thus, the composition according to the present invention can be stored for a long period of time.

On the other hand, the composition according to the present invention can cause quick texture transformation after being applied onto the skin, and therefore, can provide effective make-up removability. Accordingly, the composition according to the present invention is useful as a cleansing product.

Hereafter, the composition according to the present invention will be described in a detailed manner.

[Fatty Acid Sugar Ester]

The composition according to the present invention comprises at least one (a) fatty acid sugar ester. If two or more (a) fatty acid sugar esters are used, they may be the same or different.

According to the present invention, the (a) fatty acid sugar ester comprises at least one sugar residue and at least one fatty acid residue.

As used herein, the term "sugar" means a compound containing several alcohol functions, with or without an aldehyde or ketone function, and which comprise at least four carbon atoms. These sugars may be monosaccharides, oligosaccharides or polysaccharides. As used herein, "sugar residue" and "fatty acid residue" refer to the portion of the sugar and fatty acid, respectively, which remains in the ester after reaction between the sugar and fatty acid. Synonymously, one skilled in the art can refer to fatty acid sugar ester as an ester of a sugar and a fatty acid.

Exemplary sugars that may be used according to the present invention include sucrose (or saccharose), glucose, galactose, ribose, fucose, maltose, fructose, mannose, arabinose, xylose and lactose, and derivatives thereof, such as alkyl derivatives thereof, for example methyl derivatives such as methylglucose.

The (a) fatty acid sugar ester that may be used according to the present invention may be chosen from esters or mixtures of esters of the sugars described above, and of linear and branched, saturated and unsaturated fatty acids.

The fatty acid of the (a) fatty acid sugar ester may be selected from saturated $C_{10}$-$C_{24}$ fatty acids, preferably $C_{10}$-$C_{18}$ fatty acids, and more preferably $C_{12}$-$C_{16}$ fatty acids.

The esters may be chosen from mono-, di-, tri- and tetraesters and polyesters, and mixtures thereof.

The esters may be chosen from the oleates, laurates, palmitates, myristates, behenates, cocoates, stearates, linoleates, linolenates, caprates, arachidonates, and mixtures thereof, such as, oleo-palmitate, oleo-stearate, palmito-stearate, and mixed esters.

Exemplary esters include monoesters and diesters, such as mono- and di-oleates, stearates, behenates, oleopalmitates, linoleates, linolenates and oleostearates of sugars chosen from sucrose, glucose, and methylglucose.

Examples of the (a) fatty acid sugar ester or mixtures thereof that may be mentioned include:
the products sold under the names F160®, F140®, F110®, F90®, F70® and SL40® by the company Crodesta, respectively denoting the sucrose palmitostearates formed from 73% monoester and 27% di- and triester, from 61% monoester and 39% di-, tri- and tetraester, from 52% monoester and 48% di-, tri- and tetraester, from 45% monoester and 55% di-, tri- and tetraester, from 39% monoester and 61% di-, tri- and tetraester, and sucrose monolaurate;
the products sold under the name Ryoto Sugar Esters®, for example bearing the reference B370 and corresponding to the sucrose behenate formed from 20% monoester and 80% di-triester-polyester; and
the sucrose mono-di-palmitostearate sold by the company Goldschmidt under the name Tegosoft PSE®.

Other exemplary esters include the product sold under the name Glucate Do® by the company Amerchol, which is a methylglucose dioleate.

It is preferable that the (a) fatty acid sugar ester be selected from esters of sucrose and at least one fatty acid.

The (a) fatty acid sugar ester may be selected from the group consisting of sucrose laurate, sucrose myristate, sucrose palmitate, sucrose stearate, and mixtures thereof.

The amount of the (a) fatty acid sugar ester(s) in the composition according to the present invention may be 0.001% by weight or more, preferably 0.01% by weight or more, and more preferably 0.1% by weight or more, relative to the total weight of the composition. It may be even more preferable that the amount of the (a) fatty acid sugar ester(s) in the composition according to the present invention be 1% by weight or more, relative to the total weight of the composition.

On the other hand, the amount of the (a) fatty acid sugar ester(s) in the composition according to the present invention may be 20% by weight or less, preferably 10% by weight or less, and more preferably 5% by weight or less, relative to the total weight of the composition. It may be even more preferable that the amount of the (a) fatty acid sugar ester(s) in the composition according to the present invention be 3% by weight or less, relative to the total weight of the composition.

Accordingly, the amount of the (a) fatty acid sugar ester(s) in the composition may range from 0.001% to 20% by weight, preferably from 0.01% to 10% by weight, and more preferably from 0.1% to 5% by weight, relative to the total weight of the composition. It may be even more preferable that the amount of the (a) fatty acid sugar ester(s) in the composition according to the present invention be from 1% to 3% by weight, relative to the total weight of the composition.

[Anionic Surfactant]

The composition according to the present invention comprises at least one (b) anionic surfactant selected from amino acid surfactants and taurate surfactants. If two or more such (b) anionic surfactants are used, they may be the same or different.

(Amino Acid Surfactant)

The amino acid surfactants are anionic surfactants based on amino acids or derivatives thereof. Typically, the amino acid surfactant is an anionic surfactant comprising at least one amino moiety and at least one carboxylic acid moiety which is in the form of a carboxylate. The amino acid surfactant may have two or more of amino moieties and/or two or more carboxylic acid moieties which are in the form of carboxylates.

The amino acid surfactant may preferably be selected from amino acid derivatives. The amino acid derivative may more preferably be selected from salts of amino acids and N-acylated amino acids, for example alkali metal salts and alkali earth metal salts of amino acids and N-acylated amino acids, such as sodium salts, potassium salts, magnesium salts, and calcium salts of amino acids and N-acylated amino acids.

The acyl group which forms the N-acyl moiety of the amino acid derivatives may be a $C_1$-$C_{30}$ acyl group, preferably a $C_6$-$C_{28}$ acyl group, and more preferably a $C_{12}$-$C_{24}$ acyl group.

The amino acid surfactant may even more preferably be selected from the group consisting of glutamates, N-acylated glutamates, aspartates, N-acylated aspartates, and salts thereof.

Examples of the amino acid surfactant include, but are not limited to:
  sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
  alaninates, such as sodium N-lauroyl-N-methylamidopropionate, sold under the name Sodium Nikkol Alaninate LN 30® by Nikkol or sold under the name Alanone ALE® by Kawaken, sodium cocoyl alaninates, sold under the name AMILITE® ACS-12 by Ajinomoto, or triethanolamine N-lauroyl-N-methylalanine, sold under the name Alanone ALTA® by Kawaken;
  glutamates, such as triethanolamine monococoyl glutamate, sold under the name Acylglutamate CT-12® by Ajinomoto, triethanolamine lauroyl glutamate, sold under the name Acylglutamate LT-12® by Ajinomoto, disodium glutamates, disodium stearoyl glutamate sold under the name Amisoft® HS-21P by Ajinomoto, and mixtures thereof;
  aspartates, such as disodium aspartate, disodium N-lauroyl aspartate, and mixtures thereof such as a mixture of triethanolamine N-lauroyl aspartate and triethanolamine N-myristoyl aspartate, sold under the name Asparack® by Mitsubishi; and glycine derivatives (glycinates), such as sodium N-cocoyl glycinate, sold under the names Amilite GCS-12® and Amilite GCK 12 by Ajinomoto.

(Taurate Surfactant)

The taurate surfactant is an anionic surfactant comprising at least one taurate moiety.

The taurate surfactant is preferably acyl taurate, more preferably acyl methyl taurate (i.e. N-acyl-N-methyltaurate).

The taurate surfactant may be selected from the group consisting of taurate, caproyl taurate, lauroyl taurate, myristoyl taurate, palmitoyl taurate, stearoyl taurate, oleoyl taurate, cocoyl taurate, methyl taurate, coconut oil fatty acid methyl taurate, palm kernel oil fatty acid methyl taurate, hydrogenated palm kernel oil fatty acid methyl taurate, beef tallow fatty acid methyl taurate, hydrogenated beef tallow fatty acid methyl taurate, caproyl methyl taurate, lauroyl methyl taurate, myristoyl methyl taurate, palmitoyl methyl taurate, stearoyl methyl taurate, oleoyl methyl taurate, cocoyl methyl taurate, methyltaurine cocoyl methyl taurate, and salts thereof.

Examples of the taurate surfactant include, but are not limited to:
  sodium salt of palm kernel oil methyltaurate, sold under the name Hostapon CT Patè® by Clariant;
  sodium N-cocoyl-N-methyltaurate, sold under the name Hostapon LT-SF® by Clariant or sold under the name Nikkol CMT-30-T® by Nikkol;
  sodium methyl stearoyl taurate sold under the name Nikkol SMT®; and
  sodium palmitoyl methyltaurate, sold under the name Nikkol PMT® by Nikkol.

The amount of the (b) anionic surfactant(s) selected from amino acid surfactants and taurate surfactants in the composition according to the present invention may be 0.001% by weight or more, preferably 0.01% by weight or more, and more preferably 0.05% by weight or more, relative to the total weight of the composition. It may be even more preferable that the amount of the (b) anionic surfactant(s) selected from amino acid surfactants and taurate surfactants in the composition according to the present invention be 0.1% by weight or more, relative to the total weight of the composition.

On the other hand, the amount of the (b) anionic surfactant(s) selected from amino acid surfactants and taurate surfactants in the composition according to the present invention may be 20% by weight or less, preferably 10% by weight or less, and more preferably 5% by weight or less, relative to the total weight of the composition. It may be even more preferable that the amount of the (b) anionic surfactant(s) selected from amino acid surfactants and taurate surfactants in the composition according to the present invention be 1% by weight or less, relative to the total weight of the composition.

Accordingly, the amount of the (b) anionic surfactant(s) selected from amino acid surfactants and taurate surfactants in the composition may range from 0.001% to 20% by weight, preferably from 0.01% to 10% by weight, and more preferably from 0.05% to 5% by weight, relative to the total weight of the composition. It may be even more preferable that the amount of the (b) anionic surfactant(s) selected from amino acid surfactants and taurate surfactants in the composition according to the present invention be from 0.1% to 1% by weight, relative to the total weight of the composition.

[Polyoxyalkylenated Polyol Fatty Acid Ester]

The composition according to the present invention comprises at least one (c) polyoxyalkylenated polyol fatty acid ester having an HLB value of 12 or less. If two or more (c) polyoxyalkylenated polyol fatty acid esters are used, they may be the same or different.

The (c) polyoxyalkylenated polyol fatty acid ester is an ester of a polyol and at least one fatty acid wherein the ester has at least one polyoxyalkylene moiety.

The polyoxyalkylene moiety may comprise oxyethylene units, oxypropylene units, oxybutylene units and mixtures thereof.

It is preferable that the polyoxyalkylene moiety comprise oxyethylene units, more preferably 8 or more oxyethylene groups, and even more preferably 15 or more oxyethylene groups. It is also preferable that the polyoxyalkylene moiety comprise no oxypropylene or oxybutylene unit. Thus, the (c) polyoxyalkylenated polyol fatty acid ester may preferably be polyoxyethylenated polyol fatty acid ester.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol may be a $C_2$-$C_{12}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerin or glycerols and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, and 1,5-pentanediol.

It is preferable that the polyol be glycerin.

The fatty acid may be selected from linear or branched, saturated or unsaturated fatty acids.

The fatty acid may be selected from saturated $C_{10}$-$C_{24}$ fatty acids, preferably $C_{10}$-$C_{18}$ fatty acids, and more preferably $C_{12}$-$C_{16}$ fatty acids. As examples of the saturated $C_{10}$-$C_{24}$ fatty acids, mention may be made of lauric acid, myristic acid, palmitic acid and stearic acid, as well as structural isomers thereof.

Examples of the (c) polyoxyalkylenated polyol fatty acid ester include, but are not limited to:

oxyethylenated fatty acid esters of polyols comprising at least 8 oxyethylene groups, which may comprise up to 40 oxyethylene groups, in particular oxyethylenated esters of a fatty acid comprising from 8 to 20 carbon atoms, preferably from 10 to 16 carbon atoms and better still from 10 to 14 carbon atoms and of glycerol, for instance oxyethylenated (20 OE) glyceryl triisostearate (INCI name: PEG-20 glyceryl triisostearate); and esters of a fatty acid (especially of a $C_{12}$-$C_{30}$, preferably $C_{12}$-$C_{20}$ and better still $C_{14}$-$C_{18}$ acid), in particular isostearic acid or oleic acid, and of sorbitan and/or oxyethylenated sorbitol ethers comprising at least 8 oxyethylene groups, which may comprise up to 40 oxyethylene groups, such as sorbitan trioleate 20 OE (INCI name: Polysorbate 85), sorbeth-30 tetraisostearate.

It is preferable that the (c) polyoxyalkylenated polyol fatty acid ester be selected from polyoxyethylenated or polyethoxylated polyol fatty acid esters and, more preferably, from polyoxyethylenated or polyethoxylated glyceryl fatty acid esters. Polyoxyethylenated or polyethoxylated glyceryl fatty acid esters (identified by their INCI names) include, for example, PEG-20 glyceryl triisostearate such as that sold by Nihon Emulsion as Emalex GWIS-305 and Emalex GWIS-320EX, and PEG-7 glyceryl cocoate such as that sold by Cognis as Cetiol HE, and mixtures thereof. According to one preferred embodiment of the invention the composition comprises PEG-20 glyceryl triisostearate.

The (c) polyoxyalkylenated polyol fatty acid ester may be selected from POE (polyoxyethylenated) glyceryl fatty acid esters, preferably from the group consisting of PEG-7 glyceryl cocoate, PEG-8 glyceryl isostearate, PEG-20 glyceryl tri-isostearate, PEG-20 glyceryl stearate, PEG-20 glyceryl isostearate, and mixtures thereof.

The (c) polyoxyalkylenated polyol fatty acid ester is a type of nonionic surfactant, and may have an HLB value of 6 to 12, preferably 6.5 to 11.5, and more preferably from 7 to 11.

The amount of the (c) polyoxyalkylenated polyol fatty acid ester(s) in the composition according to the present invention may be 0.001% by weight or more, preferably 0.01% by weight or more, and more preferably 0.1% by weight or more, relative to the total weight of the composition. It may be even more preferable that the amount of the (c) polyoxyalkylenated polyol fatty acid ester(s) in the composition according to the present invention be 0.5% by weight or more, relative to the total weight of the composition.

On the other hand, the amount of the (c) polyoxyalkylenated polyol fatty acid ester(s) in the composition according to the present invention may be 20% by weight or less, preferably 10% by weight or less, and more preferably 5% by weight or less, relative to the total weight of the composition. It may be even more preferable that the amount of the (c) polyoxyalkylenated polyol fatty acid ester(s) in the composition according to the present invention be 1% by weight or less, relative to the total weight of the composition.

Accordingly, the amount of the (c) polyoxyalkylenated polyol fatty acid ester(s) in the composition may range from 0.001% to 20% by weight, preferably from 0.01% to 10% by weight, and more preferably from 0.1% to 5% by weight, relative to the total weight of the composition. It may be even more preferable that the amount of the (c) polyoxyalkylenated polyol fatty acid ester(s) in the composition according to the present invention be from 0.5% to 1% by weight, relative to the total weight of the composition.

[Oil]

The composition according to the present invention comprises at least one (d) oil. If two or more (d) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The (d) oil may be a non-polar oil such as a hydrocarbon oil, a silicone oil, or the like; a polar oil such as a plant or animal oil and an ester oil or an ether oil; or a mixture thereof.

The (d) oil may be selected from the group consisting of oils of plant or animal origin, synthetic oils, silicone oils, hydrocarbon oils, and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

$$[-D''-D'---D''-D'-]$$

with D":

$$-\underset{\underset{CH_3}{|}}{\overset{\overset{CH_3}{|}}{Si}}-O-$$

and with: D':

$$-\underset{\underset{C_8H_{17}}{|}}{\overset{\overset{CH_3}{|}}{Si}}-O-$$

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3, 3'-hexatrimethylsilyloxy)neopentane; and
(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January. 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s; and
  the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

$$R_9-\underset{\underset{R_2}{|}}{\overset{\overset{R_1}{|}}{Si}}-O-\left[\underset{\underset{R_4}{|}}{\overset{\overset{R_3}{|}}{Si}}-O\right]_p-\left[\underset{\underset{R_8}{|}}{\overset{\overset{Ph}{|}}{Si}}-O\right]_q-\left[\underset{\underset{Ph}{|}}{\overset{\overset{Ph}{|}}{Si}}-O\right]_n-\left[\underset{\underset{O-Si-(R_{10})_3}{|}}{\overset{\overset{Ph}{|}}{Si}}-O\right]_m-\underset{\underset{R_7}{|}}{\overset{\overset{R_5}{|}}{Si}}-R_6$$

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups.

Mention may thus be made of the silicone KF-6017 proposed by Shin-Etsu, and the oils Silwet® L722 and L77 from the company Union Carbide.

Hydrocarbon oils may be chosen from:
- linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and
- linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It may be preferable that the (d) oil be chosen from ester oils, and more preferably from short chain ester oils such as isopropyl myristate, isopropyl palmitate, and ethyl hexyl palmitate; triglycerides such as capric/caprylic triglycerides; and sarcosinates such as lauroyl isopropyl sarcosinate.

It may be preferable that the (d) oil be chosen from hydrocarbon oils, more preferably from mineral oils, and even more preferably from paraffin oils.

The amount of the (d) oil(s) in the composition according to the present invention may be 50% by weight or more, preferably 60% by weight or more, and more preferably 70% by weight or more, relative to the total weight of the composition. It may be even more preferable that the amount of the (d) oil(s) in the composition according to the present invention be 75% by weight or more, relative to the total weight of the composition.

On the other hand, the amount of the (d) oil(s) in the composition according to the present invention may be 90% by weight or less, preferably 85% by weight or less, and more preferably 80% by weight or less, relative to the total weight of the composition.

Accordingly, the amount of the (d) oil(s) in the composition may range from 50% to 90% by weight, preferably from 60% to 85% by weight, and more preferably from 70% to 80% by weight, relative to the total weight of the composition. It may be even more preferable that the amount of the (d) oil(s) in the composition according to the present invention be from 75% to 80% by weight, relative to the total weight of the composition.

[Polyol]

The composition according to the present invention comprises at least one (e) polyol. If two or more (e) polyols are used, they may be the same or different.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol may be a $C_2$-$C_{12}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerin or glycerols and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, and 1,5-pentanediol.

It is preferable that the (e) polyol be selected from glycerin and glycols, more preferably that the (e) polyol be glycerin.

The amount of the (e) polyol(s) in the composition according to the present invention is 0.001% by weight or more, preferably 0.01% by weight or more, and more preferably 0.1% by weight or more, relative to the total weight of the composition. It may be even more preferable that the amount of the (e) polyol(s) in the composition according to the present invention be 1% by weight or more, relative to the total weight of the composition.

On the other hand, the amount of the (e) polyol(s) in the composition according to the present invention may be 20% by weight or less, preferably 15% by weight or less, and more preferably 10% by weight or less, relative to the total weight of the composition.

Accordingly, the amount of the (e) polyol(s) in the composition may range from 0.001% to 20% by weight, preferably from 0.01% to 15% by weight, and more preferably from 0.1% to 10% by weight, relative to the total weight of the composition. It may be even more preferable that the amount of the (e) polyol(s) in the composition according to the present invention be from 1% to 10% by weight, relative to the total weight of the composition.

[Water]

The composition according to the present invention comprises (f) water.

The amount of the (f) water in the composition according to the present invention is 0.001% by weight or more, preferably 0.01% by weight or more, and more preferably 0.1% by weight or more, relative to the total weight of the composition. It may be even more preferable that the amount of the (f) water in the composition according to the present invention be 1% by weight or more, relative to the total weight of the composition.

On the other hand, the amount of the (f) water in the composition according to the present invention may be 20% by weight or less, preferably 15% by weight or less, and more preferably 10% by weight or less, relative to the total weight of the composition. It may be even more preferable that the amount of the (f) water in the composition according to the present invention be 5% by weight or less, relative to the total weight of the composition.

Accordingly, the amount of the (f) water in the composition according to the present invention may range from 0.001% to 20% by weight, preferably from 0.01% to 15% by weight, and more preferably from 0.1% to 10% by weight, relative to the total weight of the composition. It may be even more preferable that the amount of the (f) water in the composition according to the present invention be from 1% to 5% by weight, relative to the total weight of the composition.

[Other Ingredients]

The composition according to the present invention may also include at least one optional or additional ingredient.

The amount of the optional or additional ingredient(s) is not limited, but may be from 0.01% to 30% by weight, preferably from 0.1% to 20% by weight, and more preferably from 1% to 10% by weight, relative to the total weight of the composition according to the present invention.

The optional or additional ingredient(s) may be selected from the group consisting of cationic, anionic, nonionic or amphoteric polymers; cationic, anionic, nonionic or amphoteric surfactants, other than the above ingredients (a) to (c); thickeners; peptides and derivatives thereof; protein hydrolyzates; swelling agents and penetrating agents; suspending agents; sequestering agents; opacifying agents; dyes; sunscreen agents; vitamins or provitamins; fragrances; preservatives, co-preservatives, stabilizers; and mixtures thereof.

The composition according to the present invention may include at least one organic solvent other than the (e) polyol. The organic solvent(s) may then be present in a concentration of from 0.01% to 30% by weight, preferably from 0.1% to 20% by weight, and more preferably from 1% to 15% by weight, relative to the total weight of the composition.

The pH of the composition according to the present invention may be adjusted to the desired value using acidifying or basifying agents commonly used in cosmetics.

The composition according to the present invention is preferably acidic. Therefore, it is preferable that the pH of the composition be from 1 to 6, more preferably from 2 to 5, and even more preferably from 2 to 4.

Among the acidifying agents, mention may be made, by way of example, of mineral acids such as hydrochloric acid, ortho-phosphoric acid, and sulfuric acid Among the basifying agents, mention may be made, by way of example, of ammonium hydroxide, alkali metal carbonates, alkanolamines such as mono-, di- and triethanolamines and also their derivatives, sodium or potassium hydroxide and compounds of the formula below:

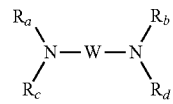

wherein

W denotes an alkylene such as propylene optionally substituted by a hydroxyl or a $C_1$-$C_4$ alkyl radical, and $R_a$, $R_b$, $R_c$ and $R_d$ independently denote a hydrogen atom, an alkyl radical or a $C_1$-$C_4$ hydroxyalkyl radical, which may be exemplified by 1,3-propanediamine and derivatives thereof. Sodium or potassium hydroxide is preferable, because this can also function to form in situ a buffering agent.

The acidifying or basifying agent may be used in an amount ranging from 0.001 to 15% by weight, preferably from 0.01 to 10% by weight, and more preferably from 0.1 to 5% by weight, relative to the total weight of the composition.

[Preparation]

The composition according to the present invention can be prepared by mixing the ingredients (a) to (f), as essential ingredients, as well as optional ingredient(s), as explained above.

It is preferable that the composition according to the present invention be prepared based on D-phase technology. Thus, for example, the ingredients (a) to (c), (e) and (f) are mixed to form a D-phase, and then the D-phase can be diluted with the ingredient (d).

The method and means to mix the above essential ingredients as well as optional ingredients are not limited. Any conventional method and means can be used to mix the above essential ingredients as well as optional ingredients to prepare the composition according to the present invention.

[Form]

The composition according to the present invention can be in the form of a gel and the like. Thus, the composition according to the present invention can be viscous before being used.

The composition according to the present invention may preferably be transparent or translucent. Also, the composition according to the present invention may preferably be gelled, and therefore, it can exhibit very good stability when, for example, being stored.

By "gelled" is meant the fact that the gelled composition according to the present invention does not run, in other words that it has a certain viscosity. The viscosity of the composition according to the present invention may range, for example, from 5 to 190 poises (0.5 to 19 Pa·s), preferably from 5 to 150 poises (0.5 to 15 Pa·s) and more preferably from 10 to 120 poises (1 to 12 Pa·s), this viscosity being measured using a Rheomat 180 viscometer at a shear rate of 200 s$^{-1}$ and at 25° C.

[Cosmetic Process]

The composition according to the present invention may preferably be used as a cosmetic composition. The cosmetic composition may be a skin cosmetic composition, such as a skin cleansing composition. The skin here encompasses face skin, neck skin, and the scalp. The composition according to the present invention may also be used for mucosae such as the lips, and the like.

In particular, the composition according to the present invention may be intended for application onto a keratin substance such as the skin or lips, preferably the skin. Thus, the composition according to the present invention can be used for a cosmetic process for the skin or lips, preferably a cleansing process for the skin or lips, and more preferably a cleansing process for the skin to remove make-up on the skin or lips.

The cosmetic process or cosmetic use for a keratin substance such as the skin and the lips, according to the present invention comprises, at least, the step of applying onto the keratin substance the composition according to the present invention.

EXAMPLES

The present invention will be described in a more detailed manner by way of examples. However, these examples should not be construed as limiting the scope of the present invention.

Example 1 and Comparative Examples 1-3

[Preparation]

Each of the cleansing cosmetic compositions according to Example 1 (Ex. 1) and Comparative Examples 1-3 (Comp. Ex. 1 to Comp. Ex. 3) was prepared by mixing the ingredients shown in column "A" in Table 1 at room temperature to form a D-phase, mixing the ingredients shown in column "B" at around 80° C. to form an oily phase, and then diluting the D-phase with the oily phase at room temperature. The numerical values for the amounts of the ingredients are all based on "% by weight" as active raw materials.

TABLE 1

| | | Ex . 1 | Comp. Ex. 1 | Comp. Ex. 2 | Comp. Ex. 3 |
|---|---|---|---|---|---|
| A | Sucrose Laurate | 0.65 | 0.65 | 0.65 | 0.65 |
| | Sucrose Palmitate | 0.65 | 0.65 | 0.65 | 0.65 |
| | PEG-20 Glyceryl Triisostearate | 0.7 | — | — | 0.7 |
| | Sodium Methyl Stearoyl Taurate | 0.2 | — | 0.2 | — |
| | Glycerin | 5 | 5 | 5 | 5 |
| | Propanediol | 3 | 3 | 3 | 3 |
| | Hydrogenated Starch Hydrolysate | 6 | 6 | 6 | 6 |
| | Water | 4.455 | 4.455 | 4.455 | 4.455 |
| | Sodium Hydroxide | 0.045 | 0.045 | 0.045 | 0.045 |
| B | Ethylhexyl Palmitate | QS 100 | QS 100 | QS 100 | QS 100 |
| | Caprylic/Capric Triglyceride | 4.5 | 4.5 | 4.5 | 4.5 |
| | Tocopherol | 0.1 | 0.1 | 0.1 | 0.1 |
| | Fragrance | 0.5 | 0.5 | 0.5 | 0.5 |
| Texture Transformation Speed | | Good | Good | Poor | Fair |
| Stability | | Good | Poor | Good | Poor |

[Evaluations]

(Texture Transformation Speed)

Five professional panelists evaluated the texture transformation speed of the compositions according to Example 1 and Comparative Examples 1-3. Each panelist took 0.2 g of each composition and applied it circularly on their hands. They evaluated it by counting the number of times rubbing was required until texture transformation occurred. The number of times of rubbing was classified in the following three categories based on the average thereof.

Good: Less than 15 times
Fair: 15 to 30 times
Poor: More than 30 times

The results are shown in Table 1.

(Stability)

Each of the compositions according to Example 1 and Comparative Examples 1-3 was filled into four transparent glass bottles, and the four glass bottles were held under temperature conditions of 4° C., 25° C., 40° C. and 45° C. for 2 months. The aspect of each bottle was then investigated for the degree of change (color, odor, pH, viscosity and emulsion state), and evaluated by the following criteria.

Good: No separation occurred
Poor: Separation occurred

The results are shown in Table 1.

It is clear from Table 1 that the composition according to Example 1 which comprises (a) fatty acid sugar ester(s), (b) anionic surfactant(s) selected from amino acid surfactants and taurate surfactants, (c) polyoxyalkylenated polyol fatty acid ester(s), (d), oil(s), (e) polyol(s), and (f) water, can be stable and provide quick texture transformation.

On the other hand, the composition according to Comparative Example 1 which lacks the above ingredients (b) and (c) is not stable. The composition according to Comparative Example 2 which lacks the above ingredient (c) cannot provide quick texture transformation. The composition according to Comparative Example 3 which lacks the above ingredient (b) is not stable, and cannot provide quick texture transformation.

The invention claimed is:

1. A composition, comprising:
   (a) at least one fatty acid sugar ester;
   (b) at least one anionic surfactant selected from taurate surfactants;
   (c) at least one polyoxyalkylenated polyol fatty acid ester having an HLB value of 12 or less;
   (d) at least one oil;
   (e) at least one polyol; and
   (f) water,
   wherein the amount of the (b) taurate surfactant in the composition ranges from 0.05% to 5% by weight, relative to the total weight of the composition,
   wherein the amount of the (c) polyoxyalkylenated polyol fatty acid ester in the composition ranges from 0.1% to 5% by weight, relative to the total weight of the composition,
   wherein the amount of the (d) oil in the composition ranges from 50% to 90% by weight, relative to the total weight of the composition,
   wherein the amount of the (f) water in the composition ranges from 0.001% to 5% by weight, relative to the total weight of the composition,
   wherein the (c) polyoxyalkylenated polyol fatty acid ester is selected from PEO glyceryl fatty acid esters, and
   wherein the composition is in a form of a gel.

2. The composition according to claim 1, wherein the fatty acid of the (a) fatty acid sugar ester is selected from saturated C10-C24 fatty acids.

3. The composition according to claim 1, wherein the (a) fatty acid sugar ester is selected from the group consisting of sucrose laurate, sucrose myristate, sucrose palmitate, sucrose stearate, and mixtures thereof.

4. The composition according to claim 1, wherein the amount of the (a) fatty acid sugar ester in the composition ranges from 0.001% to 20% by weight, relative to the total weight of the composition.

5. The composition according to claim 1, wherein the taurate surfactant is selected from the group consisting of taurate, caproyl taurate, lauroyl taurate, myristoyl taurate, palmitoyl taurate, stearoyl taurate, oleoyl taurate, cocoyl taurate, methyl taurate, coconut oil fatty acid methyl taurate, palm kernel oil fatty acid methyl taurate, hydrogenated palm kernel oil fatty acid methyl taurate, beef tallow fatty acid methyl taurate, hydrogenated beef tallow fatty acid methyl taurate, caproyl methyl taurate, lauroyl methyl taurate, myristoyl methyl taurate, palmitoyl methyl taurate, stearoyl methyl taurate, oleoyl methyl taurate, cocoyl methyl taurate, methyltaurine cocoyl methyl taurate, and salts thereof.

6. The composition according to claim 1, wherein the (c) polyoxyalkylenated polyol fatty acid ester has an HLB value of 6 to 12.

7. The composition according to claim 1, wherein the amount of the (d) oil in the composition ranges from 60% to 85% by weight, relative to the total weight of the composition.

8. The composition according to claim 1, wherein the amount of the (e) polyol in the composition ranges from 0.001% to 20% by weight, relative to the total weight of the composition.

9. The composition according to claim 1, wherein the composition is a cosmetic composition.

10. A cosmetic process for a keratin substance, comprising applying to the keratin substance the composition according to claim 1.

11. The cosmetic process according to claim 10, further comprising causing texture transformation of the composition on the keratin substance.

12. The cosmetic process according to claim 11, further comprising removing a makeup on the keratin substance.

13. The composition according to claim 1, wherein the (c) polyoxyalkylenated polyol fatty acid ester is selected from the group consisting of PEG-7 glyceryl cocoate, PEG-8 glyceryl isostearate, PEG-20 glyceryl tri-isostearate, PEG-20 glyceryl stearate, PEG-20 glyceryl isostearate, and mixtures thereof.

* * * * *